(12) United States Patent
Haight

(10) Patent No.: US 8,415,620 B2
(45) Date of Patent: Apr. 9, 2013

(54) DETERMINING DOPING TYPE AND LEVEL IN SEMICONDUCTING NANOSTRUCTURES

(75) Inventor: Richard A. Haight, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 156 days.

(21) Appl. No.: 12/685,129

(22) Filed: Jan. 11, 2010

(65) Prior Publication Data
US 2011/0168885 A1 Jul. 14, 2011

(51) Int. Cl.
*H01J 47/00* (2006.01)
(52) U.S. Cl. ........................... 250/305
(58) Field of Classification Search .......... 250/492.1, 250/492.2, 423 P, 305
See application file for complete search history.

(56) References Cited

U.S. PATENT DOCUMENTS

| | | | |
|---|---|---|---|
| 3,770,337 A * | 11/1973 | Merren | 250/282 |
| 4,755,049 A | 7/1988 | Bomback et al. | |
| 5,705,403 A | 1/1998 | Baek et al. | |
| 6,788,076 B2 | 9/2004 | Howland | |
| 6,890,772 B2 | 5/2005 | Liu et al. | |
| 6,950,190 B2 | 9/2005 | Smith | |
| 7,029,933 B2 | 4/2006 | Wee et al. | |
| 7,034,295 B2 * | 4/2006 | Koshikawa et al. | 250/306 |
| 7,504,838 B1 | 3/2009 | Zhao et al. | |
| 7,569,816 B1 * | 8/2009 | Browning | 250/305 |
| 7,608,838 B1 * | 10/2009 | Browning | 250/396 ML |
| 7,718,961 B1 * | 5/2010 | Browning | 250/306 |
| 7,830,089 B2 * | 11/2010 | Murano et al. | 313/506 |
| 7,880,377 B2 * | 2/2011 | Orita et al. | 313/503 |
| 7,915,146 B2 * | 3/2011 | Haight et al. | 438/478 |
| 8,057,908 B2 * | 11/2011 | Marks et al. | 428/447 |
| 2008/0283743 A1* | 11/2008 | deCecco et al. | 250/305 |
| 2009/0102019 A1 | 4/2009 | Haight et al. | |
| 2009/0183994 A1 | 7/2009 | Misra et al. | |

OTHER PUBLICATIONS

"Carrier Concentration at Thermal Equilibrium." Physics of Semi Conductor Devices, New York: Wiley-Interscience, 1981.*
Olthof, S., et.al., "Photoelectron spectroscopy study of systematically varied doping concentrations in an organic semiconductor layer using a molecular p-dopant" Journal of Applied Physics 106, 103711 (2009).*
Haight et al., "Photoelectron spectroscopy of individual nanowires of Si and Ge," Appl. Phys. Lett. 91, 233116 (2007).*
Carrier Concentration at Thermal Equilibrium. Physics of Semi Conductor Devices, New York: Wiley-Interscience, 1981.*
R. Haight et al., "Photoelectron spectroscopy of individual nanowires of Si and Ge", Appl. Phys. Lett. 91, 233116 (2007), published online Dec. 7, 2007.
D. E. Perea et al., "Direct measurement of dopant distribution in an individual vapour-liquid-solid nanowire", Nature Nanotechnology 4, pp. 315-319 (2009), online: Mar. 29, 2009.
"Carrier Concentration at Thermal Equilibrium." Physics of Semi Conductor Devices. New York: Wiley-Interscience, 1981. 16-27.

(Continued)

*Primary Examiner* — David A Vanore
*Assistant Examiner* — Wyatt Stoffa
(74) *Attorney, Agent, or Firm* — Cantor Colburn LLP; Vazken Alexanian

(57) ABSTRACT

Systems and methods for determining doping type and level in semiconducting nanostructures include generating light from a laser source, directing the light on the device via an extended microscope, collecting electrons emitted from the device in an electron analyzer and calculating the doping type and level of the device.

20 Claims, 6 Drawing Sheets

OTHER PUBLICATIONS

K. Tanaka et al, "Distinct Fermi-Momentum-Dependent Energy Gaps in Deeply Underdoped Bi2212", Science Dec. 22, 2006: vol. 314. No. 5807, pp. 1910-1913, pub. Sci Exp. Nov. 16, 2006.

B. A. Wacaser et al., "Growth System, Structure, and Doping of Aluminum-Seeded Epitaxial Silicon Nanowires", Nano Lett., 2009, 9 (9), pp. 3296-3301, Jul. 29, 2009.

P. J. Wellman et al., "Determination of doping levels and their distribution in SiC by optical techniques", Materials Science and Engineering B102 (2003) pp. 262-268.

* cited by examiner

DETERMINING DOPING TYPE AND LEVEL IN SEMICONDUCTING NANOSTRUCTURES

BACKGROUND

The present invention relates to semiconducting devices, and more specifically, to methods and systems for determining doping type and level in individual semiconducting nano structures.

A nanowire is a nanostructure, which can have a diameter on the order of nanometers. Nanowires exhibit various quantum mechanical properties due to the quantum confinement resulting from the diameter of the nanowire. As such, nanowires can be implemented in many technologies including but not limited to electronic, opto-electronic and nanoelectromechanical devices, as additives in advanced composites, for metallic interconnects in nanoscale quantum devices, as field-emitters and as leads for biomolecular nanosensors. In order to control the quantum mechanical (and other electrical) properties, the nanowires can be doped by various techniques, including diffusion and implantation. While doping techniques can in theory result in a known doping level, the dopants do not always incorporate into the nanowire structure. Electrical measurements can be made on the nanowire to determine electrical properties of the nanowire. However, while electrical measurements can be made on individual nanowires, extracting doping levels can be problematic due to contact issues. Doping levels are one of the technological pieces of information necessary to the formation and proper performance of a device such as a digital switch or sensor, in which the nanowire is implemented. In addition, doping level is an enabler to making a nanoscale device operate as, for example, a field effect transistor. As discussed above, accurate, controllable doping in nanostructures is, in itself difficult to achieve. As a result it is necessary to be able to measure the doping levels of nanostructures in both the development and eventual manufacturing stages.

SUMMARY

Exemplary embodiments include a method for determining a doping type and level of a device, the method including generating light from a laser source, directing the light on the device via an extended microscope, collecting electrons emitted from the device in an electron analyzer and calculating the doping type and level of the device.

Additional exemplary embodiments include a method for determining doping type and level in a nanostructure, the method including generating laser light with an energy corresponding to an energetic separation related to a dopant in the nanostructure, focusing the laser light on the nanostructure to cause photoemission of electrons from the nanostructure and energy analyzing the electrons to determine the doping type and the doping level of the dopant.

Further exemplary embodiments include a system for determining doping type and level of a nanostructure, the system including a light source configured to generate and direct light on the nanostructure, the light source having an energy corresponding to an energetic separation related to a dopant in the nanostructure, an extended microscope configured to image the nanostructure and to transmit the light to the nanostructure and an electron analyzer configured to receive electrons emitted from the nanostructure and to determine the dopant type and level of the nanostructure.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Exemplary embodiments include systems and methods for determining doping type, doping levels, and work function of individual isolated nanostructures including but not limited to nanowires, nanodots, and nanorods. As such, the dopant type and level of individual semiconductor nanostructures can be determined. In exemplary embodiments, photoelectron spectroscopy can be implemented on single isolated nanostructures. For illustrative purposes, single isolated semiconductor nanowires are discussed herein. As discussed above, it is appreciated that other nanostructures can be implemented in other exemplary embodiments. In exemplary embodiments, energetic light can be focused on a single isolated semiconducting nanowire and the photoemission spectrum can be collected to determine the doping type and doping level. From the identification of the valence band maximum (VBM) or $E_V$ in the spectrum and, separately, determination of the Fermi level ($E_f$) of the system, the energetic separation $E_f$–VBM is determined. Once the $E_f$–VBM is determined, the doping level can then be calculated as further described herein. In exemplary embodiments, for p-type devices, the energetic separation between the valence band maximum ($E_V$) and the Fermi level, $E_f$–$E_V$, is measured. In exemplary embodiments, for n-type devices, the energetic separation between the conduction band minimum and the Fermi level, $E_C$–$E_f$, is measured.

Figure 1:
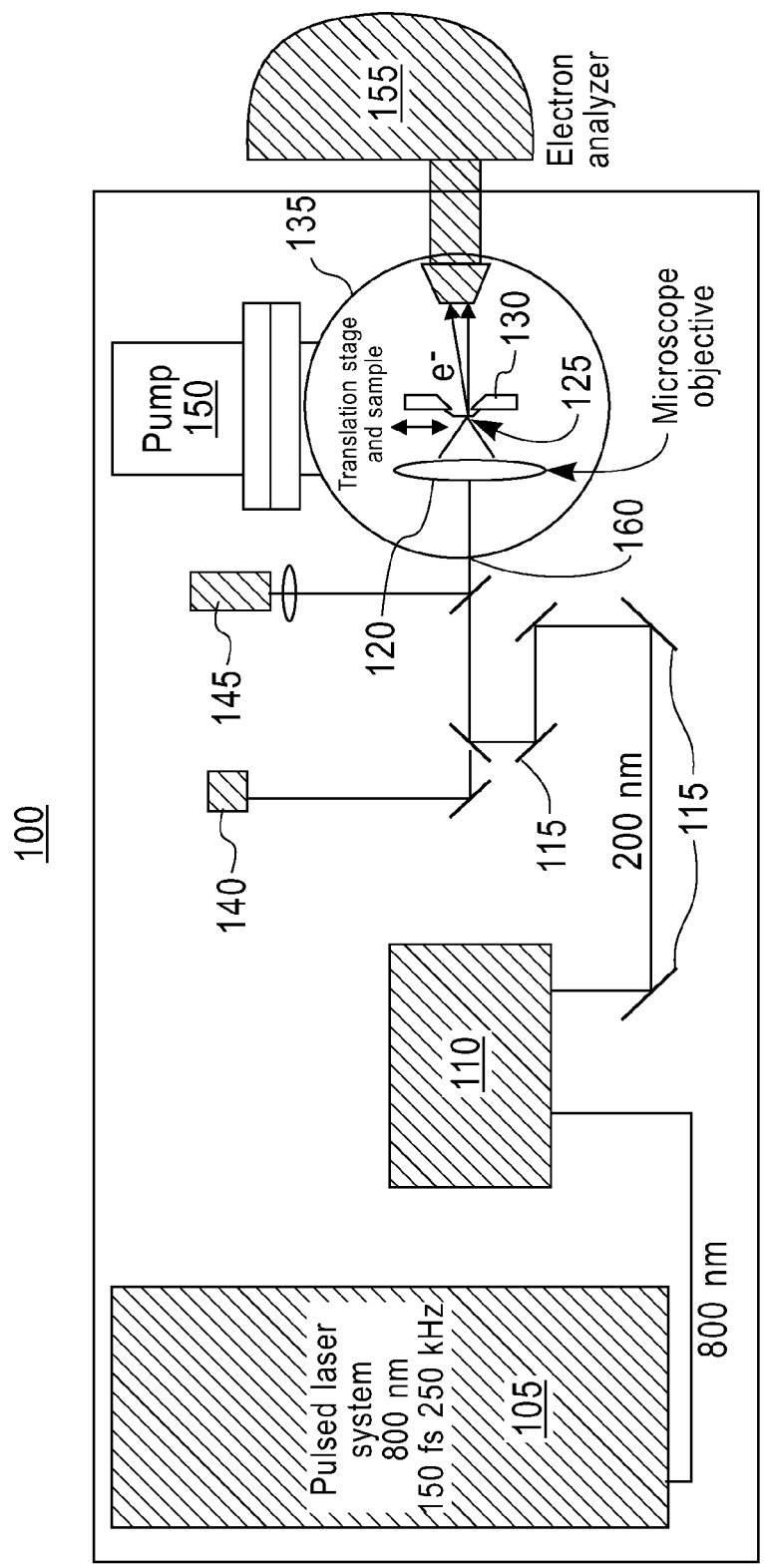
FIG. 1 illustrates an exemplary system for measuring doping type and doping levels in nanostructures.

FIG. 1 illustrates an exemplary system 100 for measuring doping type and doping levels in nanostructures. In exemplary embodiments, the system 100 can include a pulsed laser 105 that can include a pump laser coupled to a regenerative amplifier to produce laser light at a known wavelength, repetition rate and pulsewidth. Although many ranges of wavelengths, repetition rates and pulsewidths are contemplated, the system 100 is shown as producing laser light of 800 nm (1.55 eV) at a 250 kHz repetition rate with a pulsewidth of 150 fs. In other exemplary embodiments, other light sources can also be implemented as described herein.

The system 100 can further include an optical conversion box 110 coupled to the pulsed laser 105. In exemplary embodiments, the optical conversion box 110 can include a series of non-linear crystals that can be implemented to convert the laser light to light of a different wavelength desirable for measuring doping levels. For example, the 800 nm light can be converted to 200 nm (6.2 eV) light. Although other wavelengths are contemplated, the 200 nm wavelength corresponds to 6.2 eV, which is energetic enough to emit electrons from the relevant electronic states of the nanowires. In addition, the energies of the photoemitted electrons are low relative to the escape energy required to emit from the nanowire (e.g., <10 eV). As such, the energy of the photoemitted electrons translates to the escape depth being long relative to a diameter of the nanowire. Photon energies for photoemission can vary between 10-100 eV and the photoemitted electrons have escape depths that are less than 1 nm, hence very surface sensitive. In exemplary embodiments, the 6.2 eV energy level provides energy sufficient to enable escape of electrons at the energy levels of interest corresponding to the dopants. In other exemplary embodiments, a discharge lamp that produces such energetic light, properly filtered to yield a single wavelength near 200 nm, an ArF excimer laser operating at 193 nm (6.4 eV) or a synchrotron based light source can be implemented as light sources. As such, the system first laser generates short wavelength light, with desirable photon energies greater than 5 eV.

In exemplary embodiments, the 200 nm laser light can be guided through one or more optical guides (e.g., mirrors and windows) 115 to guide the light to a microscope objective 120. The microscope objective 120 can be any suitable lens that focuses the laser light to a desirable spot size (e.g., ~1 micron spot size at its focus). For example, the microscope objective 120 can be a Swarzchild object. The laser light is focused through the microscope objective 120 to a nanostructure (e.g., a nanowire) 125, which is previously grown onto a substrate 130 as described further herein.

In exemplary embodiments, the nanostructure 125 and the substrate 130 are imaged and positioned within a vacuum chamber 135, which can include a vacuum pump 150 to pull the desired vacuum in the vacuum chamber 135. In exemplary embodiments, the wire 125 and the substrate 130 can be positioned on a sample holder with a two-axis piezoelectric positioning stage to position the wire 125 and the substrate 130. The vacuum chamber 135 can further include a vacuum compatible window 160 configured to transmit the laser light into the vacuum chamber 135. In exemplary embodiments, the vacuum compatible window 160 can be a fused silica or any other deep ultraviolet (e.g., corresponding to wavelengths including 248 nm, 200 nm and 193 nm) transmitting material such as, but not limited to, MgF, CaF, and LiF.

In order to properly image and position the nanostructure 125 and the substrate 130, the system 100 further includes a lamp 140 and a camera 145. In exemplary embodiments, the optical paths of the lamp 140 and the camera 145 are superimposed in the same optical paths as the laser (200 nm) light, such as to mimic the path of the laser light. As such, before the laser light is generated, the lamp 140 and the camera 145 are implemented to image the nanowire 125 and the substrate 130 to ensure that the nanowire 125 is in the optical path of the laser light. In this way, the microscope objective 120, the lamp 140, and the camera 145 form an extended microscope so that the substrate 130 can be translated into position so that the nanowire 125 is at the focus of the microscope objective 120. In exemplary embodiments, the extended microscope can implement deep ultraviolet light such as 248 nm, 200 nm or 193 nm to locate the nanowire. In exemplary embodiments, imaging the nanowire 125 includes detecting scattered light in the extended microscope to determine that the nanowire 125 is properly positioned in the optical path of the laser light.

In exemplary embodiments, the system 100 can further include an electron analyzer 155 that is configured to receive photoemitted electrons (e-) from the nanowire 125 when the laser light is directed on the nanowire 125. In exemplary embodiments, the microscope objective 120, the nanowire 125, the substrate 130, and a portion of the electron analyzer 155 are disposed in the vacuum chamber 135.

Figure 2:
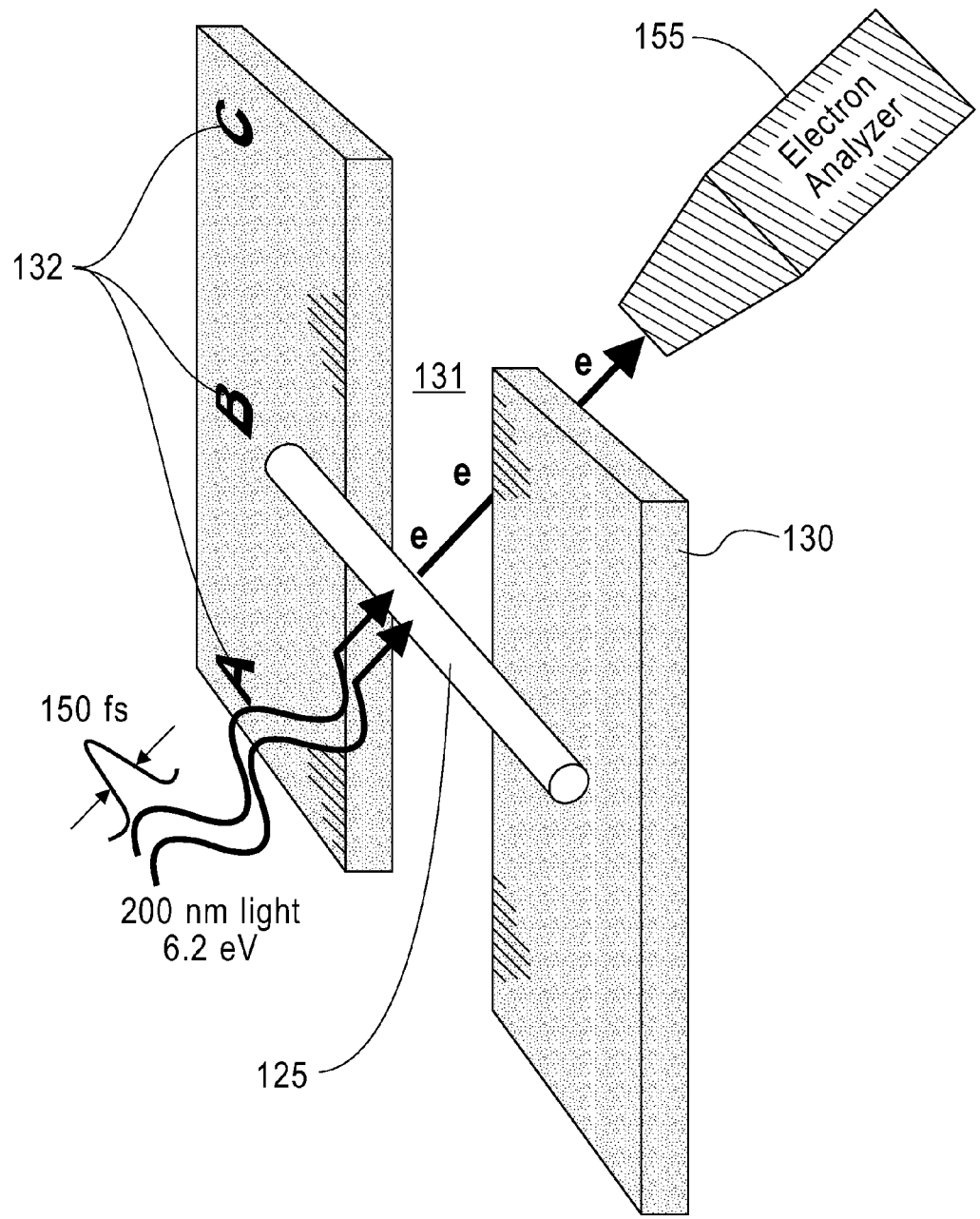
FIG. 2 illustrates a close-up perspective view of the nanowire and the substrate of FIG. 1.

FIG. 2 illustrates a close-up perspective view of the nanowire 125 and the substrate 130 of FIG. 1. In exemplary embodiments, the nanowire 125 can be grown across a slot 131 on the patterned conductive substrate 130. The nanowire 125 can be grown across the slot because the laser light is sent into the front of the nanowire 125 and the photoemitted electrons are emitted out the back of the nanowire 125. The slot 131 is etched so that the slot 131 extends completely through the substrate 130 so that the emitted electrons can transit to the analyzer 155. In exemplary embodiments, the nanowire 125 is suspended across the slot 131. In exemplary embodiments, the substrate 130 can be a thin silicon wafer, Si. In exemplary embodiments, the substrate 130 can be provided with fiducials 132 that can include numbers, letters and markings, which allow location of the nanostructure 125 as described above. In exemplary embodiments, the nanowire 125 can be grown with any suitable fabrication method including, but not limited to vapor liquid solid method (VLS), in which Si in the form of silane forms a eutectic, a liquid amalgam with a gold catalyst. As the nanowire 125 grows, the gold then precipitates out. The doping atoms are incorporated from the gas phase by being introduced as phosphene, arsene or diborane.

Figure 3:
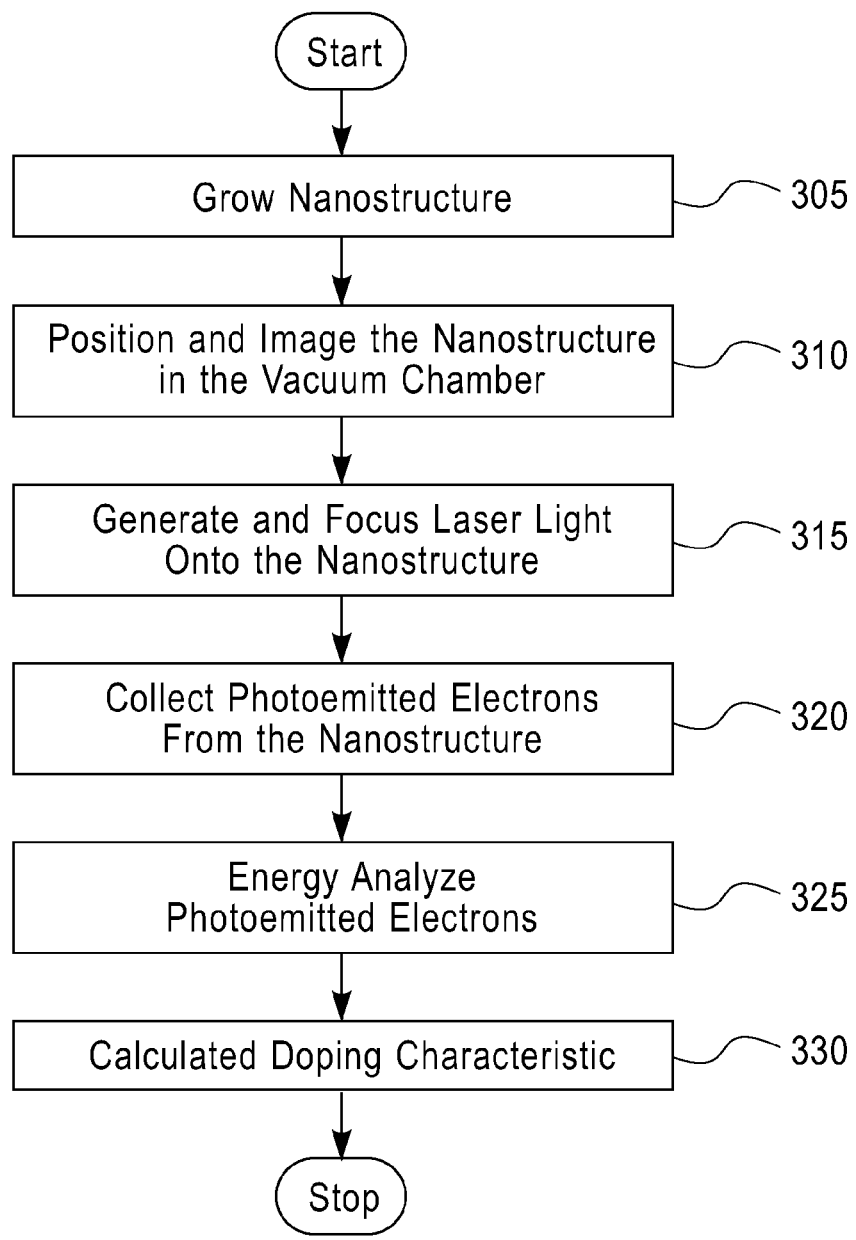
FIG. 3 illustrates a flowchart of a method for measuring doping type and doping levels in nanostructures in accordance with exemplary embodiments.

FIG. 3 illustrates a flowchart of a method 300 for measuring doping type and doping levels in nanostructures in accordance with exemplary embodiments. At block 305, the nanostructure 125 is grown on the substrate 130 as described herein. At block 310, the nanostructure 125 is imaged and positioned within the vacuum chamber 135 as described herein. At block 315, the laser light is generated as described herein. In exemplary embodiments, the laser light is focused by the microscope objective 120 to a small spot on the front surface of the isolated nanostructure 125. The focused energetic light is then used to photoemit electrons which emerge from the back side of the nanostructure 125. At block 320, the photoemitted electrons are collected at the analyzer 155. At block 325, the photoemitted electrons are energy analyzed. In exemplary embodiments, the analyzer 155 can be previously calibrated to determine a Fermi level of the system 100 by generating a photoemission spectrum from a clean metal. With the Fermi level of the system 100 established, the photoemission spectrum is collected from the nanostructure 125. Photoemission spectra are generated within just a few minutes of light exposure and the valence band maximum is easily measured relative to the Fermi level. From this energetic separation the doping level and work function of the nanostructure is determined. As such, at block 330, the doping characteristic (e.g., doping type and doping level) is calculated. In exemplary embodiments, a valence band maximum is then determined from the photoemission spectrum. The energetic separation between the valence band maximum ($E_V$) and the Fermi level can then be measured. The doping level for a p-doped nanostructure is then determined from the following equation:

$$N_A = N_V e^{-[E_f - E_V]/kT} \quad 1)$$

where $N_A$ is, for this case an acceptor (p-type) doping density, $N_V$ is the effective density of valence band states for the specific semiconductor, $E_f - E_V$ is the energetic separation between the valence band maximum and the Fermi level, k is the Boltzmann constant, and T is temperature in Kelvin. $E_V$ and $E_f$ are measured in the system 100 as described.

To measure the doping level for an n-doped nanostructure, equation 1 can be rewritten as:

$$N_D = N_C e^{-[E_c - E_f]/KT} \qquad 2)$$

where $N_D$ is the donor (n-type) doping density, $N_C$ is the effective conduction band density of states for the specific semiconductor and $E_C$ is the energy of the conduction band minimum. $E_C$ is determined from the well known energy separations of the valence and conduction band edges (i.e., band gap) for semiconductors.

EXAMPLES

Figure 4:
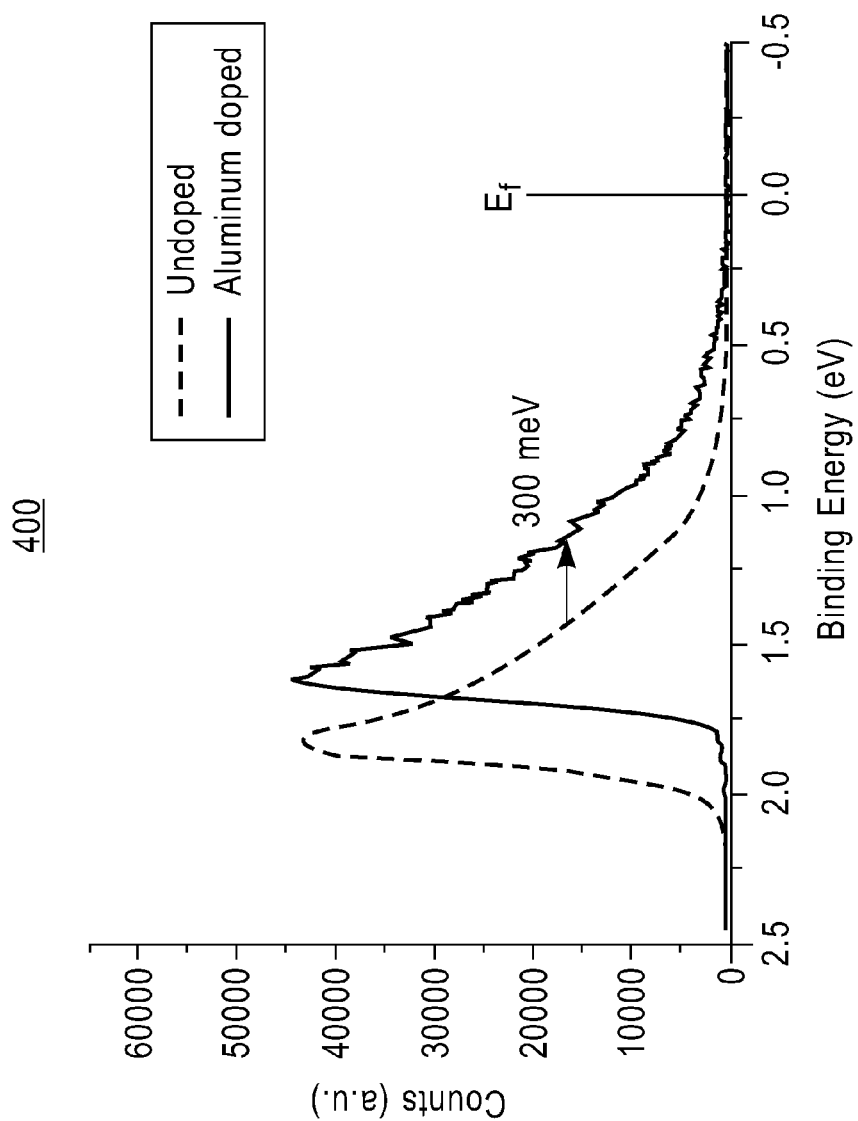
FIG. 4 illustrates an example of a plot of counts versus binding energy.
Figure 5:
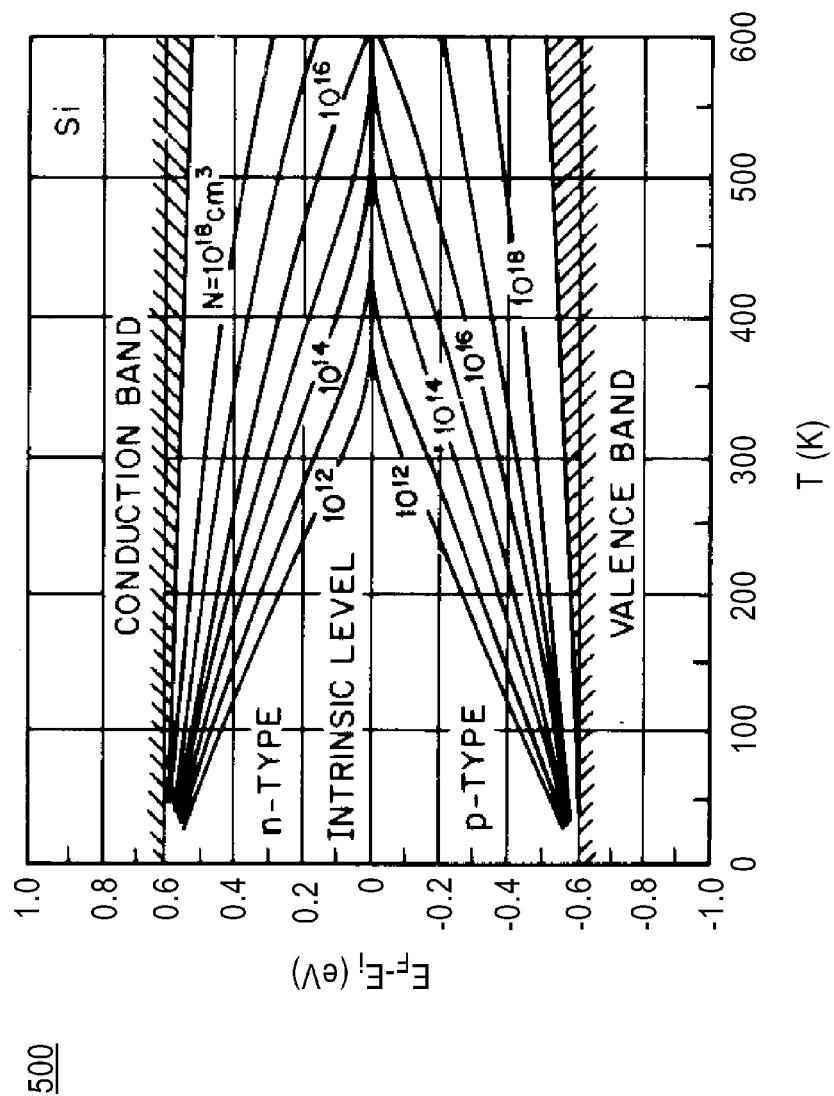
FIG. 5 illustrates a table from which doping level can be extracted from known energetic separations at known temperatures.

FIG. 4 illustrates a plot 400 of counts versus binding energy. The example in FIG. 4 illustrates an implementation to determine doping level. In the example, the counts refer to the number of electrons counted in each energy bin collected by the electron analyzer, which can be considered the intensity of the photoemission. For purposes of the example, a.u. refers to arbitrary units. In the example, a nanowire is grown with an aluminum catalyst. Incorporation of the aluminum during growth makes the nanowire p-doped. FIG. 4 illustrates a 300 meV shift of the valence edge toward $E_f$, that is, $E_f - E_v$. As such, knowing $N_V$, the doping density $N_A$, can be calculated from equation 1, which corresponds a doping level of 1 e17/cm3. FIG. 5 illustrates a table 500 from which doping level can be extracted from known energetic separations at known temperatures.

Figure 6:
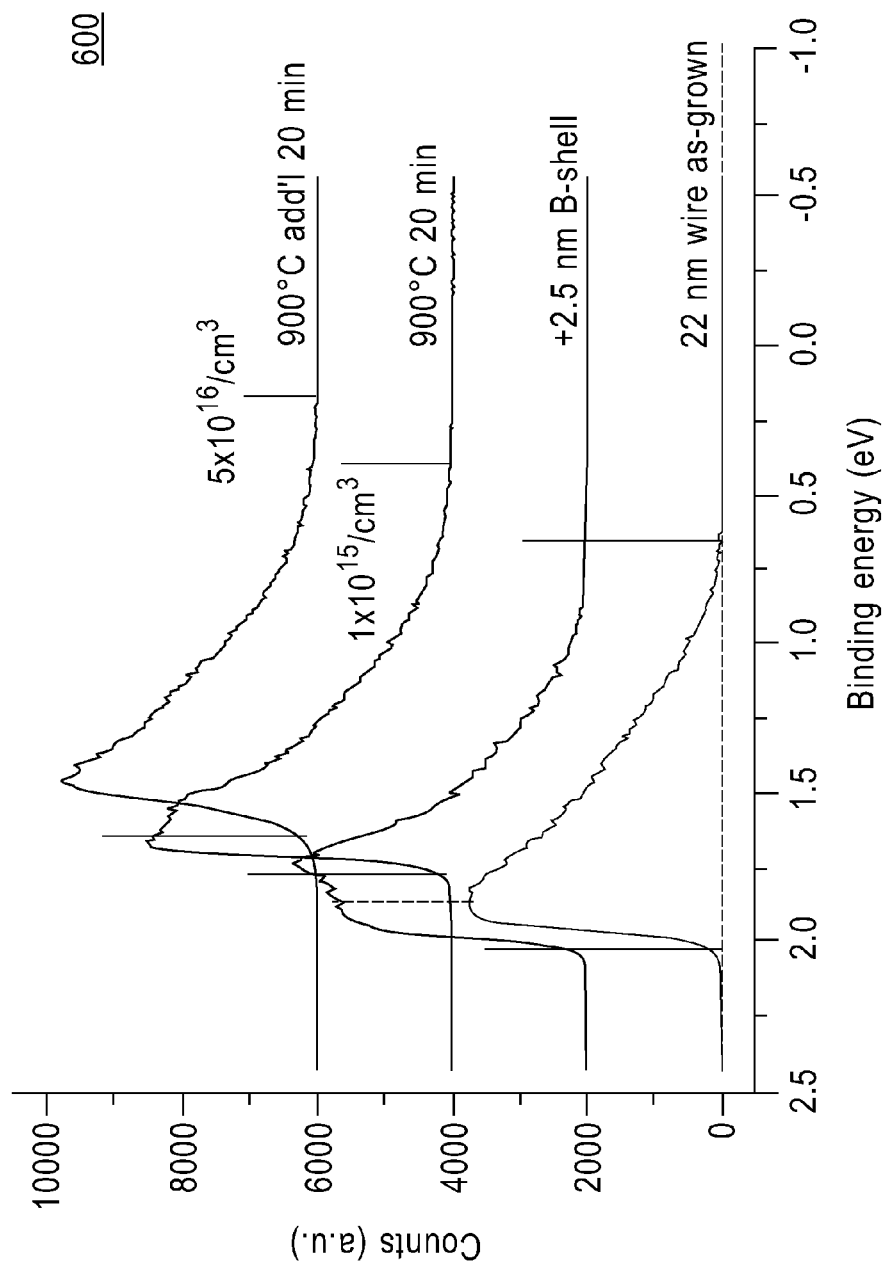
FIG. 6 illustrates an example of a plot of counts versus binding energy.

FIG. 6 illustrates an example of a plot 600 of counts versus binding energy. The example in FIG. 6 illustrates an implementation to determine doping type. In the example, a boron doped shell is grown and then the nanowire is annealed at the temperature for the duration shown. The spectra shifting to the right indicates that the Fermi level is moving closer to the valence band, which corresponds to P-type doping.

The examples in FIGS. 4 and 6 therefore illustrate that the exemplary methods and systems described herein can be implemented for a determination of doping type and level in various nanostructures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for determining a doping type and level of a device, the method comprising:
    generating light from a laser source;
    directing the light on the device via an extended microscope;
    collecting electrons photo-emitted from the device in an electron analyzer;
    measuring energy of the electrons photo-emitted from the device, to determine the Fermi level, $E_f$, of the device and at least one of the valence band maximum, $E_v$, and the conduction band minimum, $E_c$, of the device; and
    calculating a doping type and a doping level of the device to be at least one of p-type doping and n-type doping of the device,
    wherein the energy from the electrons is proportional to an energetic separation related to the doping in the device, wherein the energetic separation for p-type doping is between a valence band maximum, $E_v$, and a Fermi level, $E_f$, of the device, and the energetic separation for n-type doping is between a conduction band minimum, $E_c$, and the Fermi level, $E_f$, of the device.

2. The method as claimed in claim 1 wherein the light is laser light having energy to photoemit the electrons from the device.

3. The method as claimed in claim 1 wherein the doping type is determined by analyzing an energy shift of the electrons with respect to a Fermi level.

4. The method as claimed in claim 1 wherein the doping level is determined by comparing an energetic separation of energy associated with the electrons and a Fermi level to a known energetic separation of a known doping level.

5. The method as claimed in claim 1 wherein the electrons are energy analyzed to determine the energetic separation between the valence band maximum and the Fermi level given by $E_f - E_V$.

6. The method as claimed in claim 5 wherein a doping level, NA, of the device is calculated by, NA=NV e−[Ef−Ev]/KT, where NV is the effective density of valence band states for the specific semiconductor, k is Boltzmann constant, and T is temperature in Kelvin.

7. The method as claimed in claim 1 wherein the electrons are energy analyzed to determine the energetic separation between the conduction band minimum and the Fermi level, given by $E_C - E_f$.

8. The method as claimed in claim 7 wherein a doping level, ND, of the device is calculated by, ND=NC e−[Ec−Ef]/KT, where NC is the effective density of conduction band states for the specific semiconductor, k is Boltzmann constant, and T is temperature in Kelvin.

9. A method for determining doping type and level in a nanostructure, the method comprising:
- generating laser light with an energy corresponding to an energetic separation related to a dopant in the nanostructure;
- focusing the laser light on the nanostructure to cause photoemission of electrons from the nanostructure;
- measuring energy of the photoemission electrons from the nanostructure, to determine the Fermi level, $E_f$, of the nanostructure and at least one of the valence band maximum, $E_v$, and the conduction band minimum, $E_c$, of the nanostructure; and
- energy analyzing the photoemission electrons to calculate a doping type and a doping level of the device to be at least one of p-type doping and n-type doping of the device,
- wherein the energy from the photoemission electrons is proportional to an energetic separation related to the doping in the nanostructure, wherein the energetic separation for p-type doping is between a valence band maximum and a Fermi level of the device, and the energetic separation for n-type doping is between a conduction band minimum and the Fermi level of the nanostructure.

10. The method as claimed in claim 9 wherein energy analyzing the electrons comprises measuring the energetic separation between the valence band maximum (EV) and the Fermi level, $E_f$-$E_V$, from the electrons.

11. The method as claimed in claim 9 wherein energy analyzing the electrons comprises measuring the energetic separation between the conduction band minimum and the Fermi level, $E_C$-$E_f$, from the electrons.

12. The method as claimed in claim 9 further comprising determining the doping type by analyzing an energy shift of the electrons with respect to a Fermi level.

13. The method as claimed in claim 9 further comprising determining the doping level by comparing an energetic separation of energy associated with the electrons and a Fermi level to a known energetic separation of a known doping level.

14. A system for determining doping type and level of a nanostructure, the system comprising:
- a light source configured to generate and direct light on the nanostructure, the light source having an energy corresponding to an energetic separation related to a dopant in the nano structure;
- an extended microscope configured to image the nanostructure and to transmit the light to the nanostructure; and
- an electron analyzer configured to receive photo-emitted electrons emitted from the nanostructure and to determine the Fermi level, $E_f$, of the nanostructure and at least one of the valence band maximum, $E_v$, and the conduction band minimum, $E_c$, of the nanostructure, to calculate a doping type and a doping level of the device to be at least one of p-type doping and n-type doping of the device,
- wherein an energy of the photo-emitted electrons is proportional to an energetic separation related to the doping in the nanostructure, wherein the energetic separation for p-type doping is between a valence band maximum and a Fermi level of the nanostructure, and the energetic separation for n-type doping is between a conduction band minimum and the Fermi level of the nanostructure.

15. The system as claimed in claim 14 further comprising an optical conversion box optically coupled to the light source and to the extended microscope.

16. The system as claimed in claim 15 wherein the optical conversion box is configured to convert a wavelength of the light from the light source to a wavelength having energy to photoemit the electrons from the nanostructure.

17. The system as claimed in claim 14 wherein the extended microscope comprises:
- a microscope objective;
- a lamp in optical communication with the microscope objective; and
- a camera in optical communication with the microscope objective.

18. The system as claimed in claim 17 wherein the microscope objective, the lamp and the camera are configured to image the nanostructure.

19. The system as claimed in claim 17 wherein the microscope objective is configured to focus the light on the nano structure.

20. The system as claimed in claim 14 further comprising:
- a vacuum chamber;
- a substrate disposed in the vacuum chamber, wherein the nanostructure is disposed on the substrate; and
- a microscope objective disposed in the vacuum chamber, and configured to focus the light on the nanostructure.

* * * * *